(12) United States Patent
Bynes et al.

(10) Patent No.: US 11,858,882 B2
(45) Date of Patent: Jan. 2, 2024

(54) PREPARATION OF UREA SOLUTION AND FACILITY TO DO SO

(71) Applicant: Yara International ASA, Oslo (NO)

(72) Inventors: Adrian Bynes, Wondelgem (BE); Shreyas Amin, Terneuzen (NL); Ruud Van Belzen, Sluiskil (NL)

(73) Assignee: YARA INTERNATIONAL ASA, Oslo (NO)

( * ) Notice: Subject to any disclaimer, the term of this patent is extended or adjusted under 35 U.S.C. 154(b) by 33 days.

(21) Appl. No.: 17/633,356

(22) PCT Filed: Aug. 20, 2020

(86) PCT No.: PCT/EP2020/073288
§ 371 (c)(1),
(2) Date: Feb. 7, 2022

(87) PCT Pub. No.: WO2021/032819
PCT Pub. Date: Feb. 25, 2021

(65) Prior Publication Data
US 2022/0289669 A1 Sep. 15, 2022

(30) Foreign Application Priority Data

Aug. 20, 2019 (EP) ..................................... 19192454

(51) Int. Cl.
*C07C 273/04* (2006.01)
*B01D 3/14* (2006.01)
*C07C 273/16* (2006.01)

(52) U.S. Cl.
CPC ............ *C07C 273/04* (2013.01); *B01D 3/143* (2013.01); *C07C 273/16* (2013.01)

(58) Field of Classification Search
None
See application file for complete search history.

(56) References Cited

U.S. PATENT DOCUMENTS

| 4,539,077 A | * | 9/1985 | Jonckers | ............... | C07C 273/04 203/91 |
| 4,652,678 A |  | 3/1987 | Douwes |  |  |

(Continued)

FOREIGN PATENT DOCUMENTS

| CN | 1362404 | * | 8/2002 | ........... C07C 273/02 |
| WO | 2019093891 A1 |  | 5/2019 |  |

OTHER PUBLICATIONS

Urea (Ullmann's Encyclopedia of Industrial Chemistry, first published on Oct. 15, 2010, downloaded from https://onlinelibrary.wiley.com/doi/10.1002/14356007.a27_333.pub2 on May 3, 2023) (Year: 2010).*

(Continued)

*Primary Examiner* — Amy C Bonaparte
(74) *Attorney, Agent, or Firm* — Dilworth IP, LLC

(57) ABSTRACT

The invention relates to a method for producing a urea solution with a target urea concentration using water flows recovered from the urea production process. At least part of the water flows recovered from the urea production process are only partially purified to produce the urea solution. The invention further relates to a process condensate treatment plant to implement the method for producing a urea solution with a target urea concentration, and a urea production plant comprising such process condensate treatment plant.

21 Claims, 2 Drawing Sheets

(56) References Cited

U.S. PATENT DOCUMENTS

| | | | | |
|---|---|---|---|---|
| 5,096,599 A | * | 3/1992 | Granelli | C02F 1/025 |
| | | | | 210/903 |
| 2015/0133690 A1 | * | 5/2015 | Mennen | B01J 10/00 |
| | | | | 422/187 |
| 2017/0341951 A1 | * | 11/2017 | Nishikawa | C02F 1/20 |
| 2019/0015811 A1 | * | 1/2019 | Coloma González | B01D 5/006 |
| 2019/0177180 A1 | * | 6/2019 | Sasaki | B01D 53/78 |

OTHER PUBLICATIONS

International Search Report and Written Opinion from related PCT Application No. PCT/EP2020/073288, dated Nov. 17, 2020, 12 pages.

* cited by examiner

PREPARATION OF UREA SOLUTION AND FACILITY TO DO SO

FIELD OF THE INVENTION

The invention relates to a method for the production of a urea solution, more in particular a method for the production of a urea solution with a target urea concentration. The invention also relates to facilities to perform such methods.

BACKGROUND OF THE INVENTION

During the urea production process, $NH_3$ and $CO_2$ are reacted into a crude mixture of urea and water. The formation reactions include the formation of carbamate first, which is in a second step converted to urea and water. The two steps may be theoretically represented by the following equations (I) and (II):

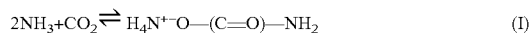
(I)

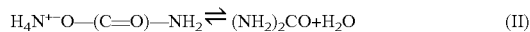
(II)

Typically, this crude urea mixture formed in the process, is separated in an aqueous urea solution and a process condensate. Typically, the process condensate is contaminated with unreacted starting material, i.e. $NH_3$ and $CO_2$ and even small amounts of urea, and this in favour of the aqueous urea solution which comprises far less unreacted starting material. The separation of the crude urea mixture in a process condensate and an aqueous urea solution can typically be seen as a purification step. The purification step might be repeated more than once, each time forming a condensate. Typically, according to environmental concerns, these process condensates cannot be discharged as such and require purification first.

The amounts of $NH_3$, $CO_2$ and urea need to be reduced or even totally removed from the process condensate before the water in the process condensate can be reused in other installations or discharged to the environment. However, this "purification process" requires large amounts of energy; typically steam is added to desorb the volatile contaminants from the water/process condensate and to hydrolyse the urea still present in the water/process condensate. Therefore, there is a demand for more energy efficient urea production methods and/or purification methods.

Even more, these purification steps can be the bottle neck in the urea production and urea production plant, restricting the flexibility of the urea production process.

The aqueous urea solution obtained after the separation of the crude urea mixture in a process condensate and an aqueous urea solution, may be further concentrated, prilled/granulated or by other means transformed into solid particles and/or diluted into a urea solution with a target urea concentration. By "target urea concentration" may be meant a predetermined urea concentration, which may be specific for a certain usage. Urea solutions with a target urea concentration are used in NOx removal processes, such as selective catalytic reduction (SRC), e.g. used to remove NOx from exhaust gasses, like diesel engines from trucks. Here, NOx is reduced to less environmental damaging nitrogen compounds, in particular to $N_2$; thereby consuming urea. A typical example of such a solution is AdBlue® or Diesel Exhaust Fluid (DEF), which is added in diesel exhausts. AdBlue® or Diesel Exhaust Fluid (DEF) is an aqueous urea solution comprising between 30.0% by weight and 35.0% by weight urea and between 65.0% by weight and 70.0% by weight water, in particular 32.5% by weight urea and 67.5% by weight water. Alternatively, such solutions may comprise between 50.0% by weight and 52.0% urea by weight. Typical, such urea solutions do not allow for many contaminants, thereby restricting the water sources that can be used to make urea solution. In particular, the $NH_3$ content of such urea solutions is at most 0.2% by weight, compared to the total weight of the urea solution.

It is one of the objects of the present invention to overcome or ameliorate one or more of the aforementioned disadvantages present in the market, or to meet any of the demands that are present in the market. In particular, the invention also provides an energy efficient method of producing a urea solution. In particular, the invention also provides more flexibility in a urea production process and/or production plant.

SUMMARY OF THE INVENTION

The present inventors have now surprisingly found that one or more of these objects can be obtained by diluting a urea solution obtained from the urea reaction process, with at least some amount of partially purified water, generated in the downstream purification process of the urea reaction process.

More in particular it has been found that using at least part of the first partially purified flow that leaves the first desorption column to dilute the first aqueous urea solution and/or the concentrated second aqueous urea solution obtained after the separation of the crude urea mixture provides in a more efficient urea production process, particularly a more energy efficient urea production process.

In a first aspect, the invention provides a method for providing a target aqueous urea composition with a target concentration urea, comprising the steps of:
a) reacting $CO_2$ and $NH_3$ in a synthesis section to form a crude urea mixture;
b) separating the crude urea mixture in an first aqueous urea solution and a process condensate using a separating section;
c) passing the process condensate through a first desorption column to provide a first partially purified flow;
d) passing at least part of the first partially purified flow through a hydrolyser to provide a second partially purified flow;
e) passing the second partially purified flow through a second desorption column to provide a purified water flow;
f) optionally concentrating the first aqueous urea solution in a pre-evaporator to provide a concentrated second aqueous urea solution;
g) mixing the first aqueous urea solution and/or the second concentrated aqueous urea solution with at least part of the first partially purified flow and at least part of the purified water flow in such a ratio to provide a target aqueous urea composition with the target concentration urea.

In some embodiments, the target aqueous urea composition has at least a upper limit for a first contaminant, the first contaminant being comprised in the first partially purified flow; and, wherein in step g) the amount of first partially purified flow used is so that in the target aqueous urea composition at least 10% to at most 100% of the limit for the first contaminant is reached.

In some embodiments, the first contaminant is ammonia.
In some embodiments, the upper limit for the first contaminant is 0.20% by weight, compared to the total weight of the target aqueous urea composition.

In some embodiments, the method further comprises the step of determining the concentration of the first contaminant in the first partially purified flow and using the concentration in determining the ratio in step g).

In some embodiments, the method further comprises the step of determining the urea concentration and/or the first contaminant in the first partially purified flow and using the concentration in determining the ratio in step g).

In some embodiments, the method further comprises the step of determining the concentration of urea in the first aqueous urea solution and/or the second aqueous urea solution and using the concentration in determining the ratio in step g).

In some embodiments, the first desorption column is placed on top of the second desorption column.

In some embodiments, step b) is performed in a condenser.

In some embodiments, the synthesis section may comprise an urea reactor, a carbamate condenser, a $NH_3$-stripper, a $CO_2$-stripper and/or a carbamate decomposer.

In some embodiments, the ratio of the first partially purified flow over the purified water flow in step g) is at least 0.5, in particular at least 0.7, in particular at least 1.0, in particular at least 1.2, in particular at least 1.3, in particular at least 1.4; the ratio being expressed as weight over weight.

In some embodiments, the ratio of first aqueous urea solution or the second urea solution over the sum of the first partially purified flow and the purified water flow, in step g) is at least 1.0, in particular at least 1.2, in particular at least 1.3, in particular at least 1.4, in particular at least 1.5, in particular at least 1.6, the ratio being expressed as weight over weight.

In a second aspect the invention provides in a process condensate treatment plant comprising:
  a first desorption column, comprising an inlet for process condensate and an outlet for a first partially purified flow;
  a hydrolyser comprising an inlet for the first partially purified flow and an outlet for a second partially purified flow;
  a second desorption column, comprising an inlet for the second partially purified flow and an outlet for a purified water flow;
wherein the process condensate treatment plant comprises a tapping point for bypassing at least partially the first partially purified flow from the hydrolyser and the second desorption column.

In some embodiments, the tapping point is provided between the outlet from the first desorption column for the first partially purified flow and the inlet to the hydrolyser for the first partially purified flow.

In a third aspect, the invention provides in an urea production plant comprising the process condensate treatment plant according an embodiment of the second aspect of the invention.

Particular embodiments of the invention are disclosed in the detailed description and appended claims. In the following passages different aspects of the invention are defined in more detail. Each aspect so defined may be combined with any other aspect or aspects unless clearly indicated to the contrary. In particular, any feature indicated as being particular or advantageous may be combined with any other feature or features indicated as being particular or advantageous. (Particular) embodiments of one aspect of the invention are also (particular) embodiments of all other aspects of the invention.

DETAILED DESCRIPTION OF THE INVENTION

Figure 1:
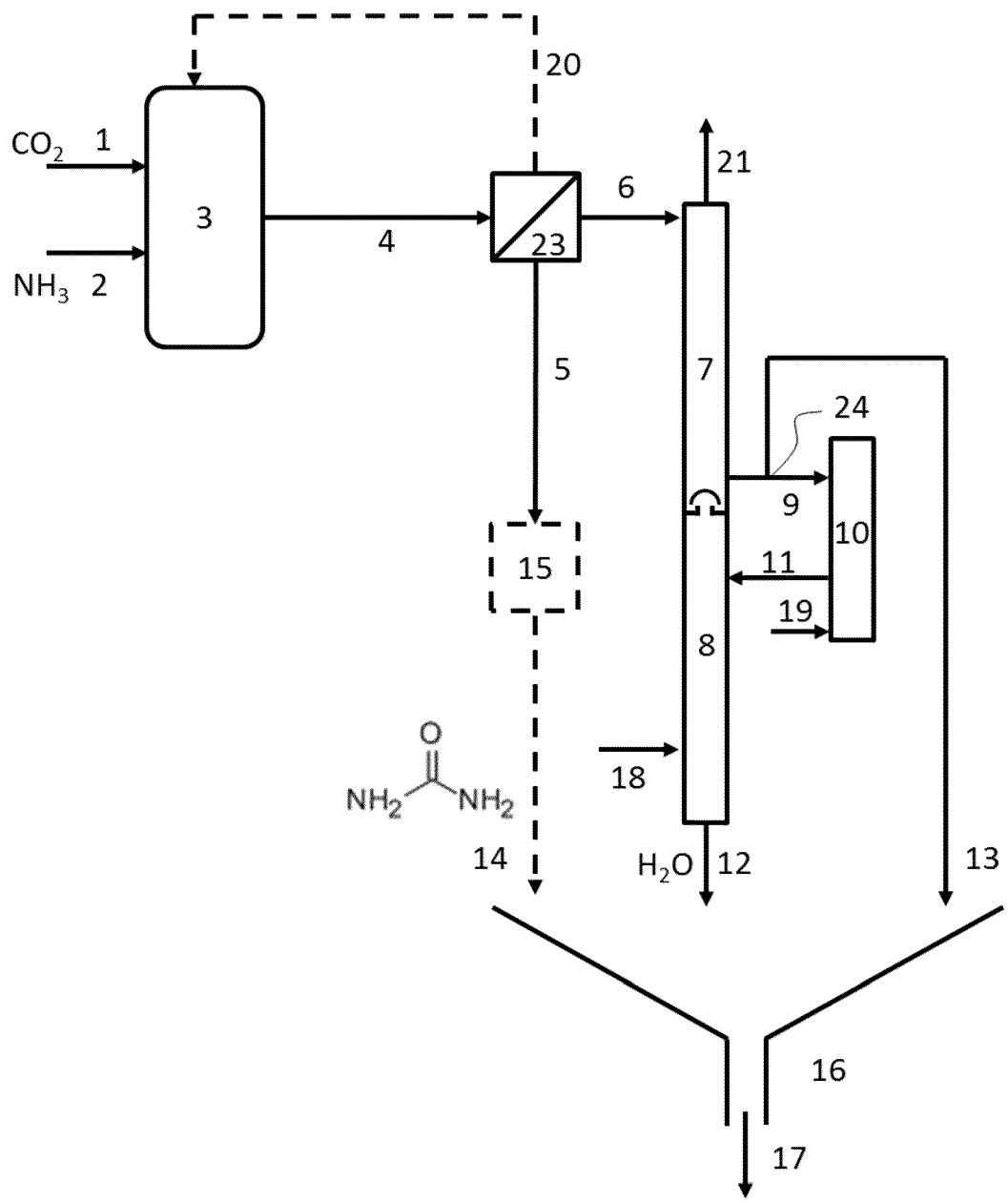
FIG. 1 provides a schematic overview of a lay-out that can be used to implement an embodiment of method of the invention. The layout includes an embodiment of the process condensate treatment plant according to the invention.

When describing the invention, the terms used are to be construed in accordance with the following definitions, unless a context dictates otherwise.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art.

As used in the specification and the appended claims, the singular forms "a", "an," and "the" include plural referents unless the context clearly dictates otherwise. By way of example, "a flow" means one flow or more than one flow.

Unless defined otherwise, all technical and scientific terms used herein have the same meaning as is commonly understood by one of skill in the art. All publications referenced herein are incorporated by reference thereto.

Throughout this application, the term "about" is used to indicate that a value includes the standard deviation of error for the device or method being employed to determine the value.

The recitation of numerical ranges by endpoints includes all integer numbers and, where appropriate, fractions subsumed within that range (e.g. 1 to 5 can include 1, 2, 3, 4 when referring to, for example, a number of elements, and can also include 1.5, 2, 2.75 and 3.80, when referring to, for example, measurements). The recitation of end points also includes the end point values themselves (e.g. from 1.0 to 5.0 includes both 1.0 and 5.0). Any numerical range recited herein is intended to include all sub-ranges subsumed therein.

The present inventors have now surprisingly found that one or more of these objects can be obtained by diluting a urea solution obtained from the urea reaction process, with at least some amount of partially purified water, generated in the downstream purification process of the urea reaction process.

More in particular, it has been found that using at least part of the first partially purified flow that leaves the first desorption column to dilute the first aqueous urea solution and/or the concentrated second aqueous urea solution obtained after the separation of the crude urea mixture provides in a more efficient urea production process, particularly a more energy efficient urea production process.

In a first aspect, the invention provides a method for providing a target aqueous urea composition with a target concentration urea, comprising the steps of:
a) reacting $CO_2$ and $NH_3$ in a synthesis section to form a crude urea mixture;
b) separating the crude urea mixture in an first aqueous urea solution and a process condensate using a separating section;
c) passing the process condensate through a first desorption column to provide a first partially purified flow;
d) passing at least part of the first partially purified flow through a hydrolyser to provide a second partially purified flow;
e) passing the second partially purified flow through a second desorption column to provide a purified water flow;
f) optionally concentrating the first aqueous urea solution in a pre-evaporator to provide a concentrated second aqueous urea solution;
g) mixing the first aqueous urea solution and/or the concentrated second aqueous urea solution with at least part of the first partially purified flow and at least part of the purified water flow in such a ratio to provide a target aqueous urea composition with the target concentration urea.

Such a method is especially advantageous when a liquid urea solution is desired instead of a dried or prilled form of urea. By "a target aqueous urea composition with a target urea concentration" may be meant a urea solution with a predetermined urea concentration, which concentration may be specific for a certain usage. A typical example of such a solution is known as AdBlue® or Diesel Exhaust Fluid (DEF) which is added in diesel exhausts. AdBlue® or Diesel Exhaust Fluid (DEF) is an aqueous urea solution comprising between 30.0% by weight and 35.0% by weight urea and between 65.0% by weight and 70.0% by weight clean water, in particular 32.5% by weight urea and 67.5% by weight clean water. Alternatively, such solutions may comprise between 50.0% by weight and 52.0% by weight. The method removes at least a part of unreacted starting materials, or contaminants such as $CO_2$ and $NH_3$ from the urea composition. Because at least some first partially purified flow is used in step g) to make the target aqueous urea composition, the fraction of first partially purified flow used does not need to pass through the hydrolyser thereby lowering the amounts of energy required that need to be added to the hydrolyser, e. g, in the form of medium pressure steam.

Furthermore, the fraction of first partially purified flow is not converted into second partially purified flow, hence less second partially purified flow needs to go through the second desorption column thereby lowering the amounts of energy required for the second desorption column e. g, in the form of low pressure steam. Hence, the more first partially purified flow used in step g) the larger the energy saving. The method further reduces the flow through the hydrolyser and the second desorption column thereby creating unused capacity, allowing more flexibility in the urea production process. This may also result in a higher amount of urea produced in a certain production plant, as a possible bottleneck formed by the hydrolyser and second desorption column is at least partially relieved.

The term "crude urea mixture" as used herein, refers to a urea mixture that is obtained after the urea formation reaction and/or carbamate decomposition reaction. It is a solution of urea $((NH_2)_2CO)$ in water and it may comprises contaminants such as carbon dioxide ($CO_2$), ammonia ($NH_3$), biuret ($H_2N-C=O-NH-(C=O)-NH_2$) and optionally ammonium carbamate ($H_4N'O-(C=O)-NH_2$), here also referred to as "carbamate". In some cases, the crude urea mixture has not yet undergone a purification step.

In particular embodiments, the crude urea mixture comprises at least 10.0% by weight urea, in particular at least 15.0% by weight urea, more in particular at least 20.0% by weight urea, even more particular at least 24.0% by weight urea, compared to the total weight of the crude urea mixture.

In particular embodiments, the crude urea mixture comprises at most 55.0% by weight urea, in particular at most 40.0% by weight urea, more in particular at most 35.0% by weight urea, even more particular at most 32.0% by weight urea, compared to the total weight of the crude urea mixture.

In particular embodiments, the crude urea mixture comprises at least 10.0% by weight to at most 55.0% by weight urea, in particular at least 15.0% by weight to at most 40.0% by weight urea, more in particular at least 20.0% by weight to at most 35.0% by weight urea, even more particular at least 24.0% by weight to at most 32.0% by weight urea, compared to the total weight of the crude urea mixture.

In some embodiments, the crude urea mixture may comprise at least 5.0% by weight urea, in particular at least 7.5% by weight urea, more in particular at least 10.0% by weight urea, compared to the total weight of the crude urea mixture.

In some embodiments, the crude urea mixture may comprise at least 5.0% by weight $CO_2$, in particular at least 7.5% by weight $CO_2$, more in particular at least 10.0% by weight $CO_2$, compared to the total weight of the crude urea mixture.

The term "process condensate" as used herein, refers to an aqueous solution that comprises higher amounts of urea then the crude urea mixture. In particular embodiments, the comprises at least 50.0% by weight urea, in particular at least 55.0% by weight urea, more in particular at least 60.0% by weight urea, even more particular at least 65.0% by weight urea, compared to the total weight of the crude urea mixture. In particular, the process condensate comprises less urea than the crude urea mixture. In particular, the process condensate comprises less than 5.0% by weight urea, in particular less than 4.0% by weight urea, more particular less than 3.0% by weight urea, even more particular less than 2.0% by weight urea, yet even more particular less than 1.0% by weight urea, the % by weight being expressed compared to the total weight of the process condensate. In some embodiments, the process condensate may comprise higher concentrations $CO_2$ than the first aqueous urea solution, particular at least 5 times higher, more particular at least 7 times higher, even more particular at least 10 times higher, yet more particular at least 15 times higher, still more particular at least 20 times higher. The process condensate may comprise at least 1.0% by weight $CO_2$, in particular at least 2.0% by weight $CO_2$, more particular at least 4.0% by weight $CO_2$, even more particular at least 6.0% by weight $CO_2$, yet even more particular at least 8.0% by weight $CO_2$, the % by weight being expressed compared to the total weight of the process condensate.

In some embodiments, the process condensate may comprise higher concentrations $NH_3$ than the first aqueous urea solution, particular at least 2 times higher, more particular at least 4 times higher, even more particular at least 6 times higher, yet more particular at least 7 times higher, still more particular at least 8 times higher. The process condensate may comprise at least 2.0% by weight $NH_3$, in particular at least 4.0% by weight $NH_3$, more particular at least 5.0% by weight $NH_3$, even more particular at least 6.0% by weight $NH_3$, yet even more particular at least 8.0% by weight $NH_3$, the % by weight being expressed compared to the total weight of the process condensate.

The term "desorption column" as used herein, refers to a column for removing at least part of the $CO_2$ in an aqueous composition such as the process condensate and/or the second partially purified flow. In some embodiments, steam is added to the desorption column, in particular low pressure (LP) steam, typically steam at least 3.0 barg to at most 10.0 barg, in particular at least 4.0 barg to at most 8.0 barg, more in particular at least 5.0 barg to at most 6.5 barg, typically at saturation temperature, like 160-170° C. In some embodiments, the desorption column(s) consume about 7 to 14 t/h LP steam. In particular, the steam and aqueous composition are contacted in the desorption column in counter current. In particular, the pressure in the desorption column is at least 1.0 barg, to at most 5.0 barg, in particular at least 1.5 barg, to at most 4.0 barg, more in particular at least 2.0 barg, to at most 3.0 barg. In some embodiments, the temperature in the bottom liquid outlet is about 146° C. while the temperature of the vapours in the top outlet is about 116° C.

The term "first partially purified flow" as used herein, refers to an aqueous flow derived from the process condensate, typically comprising lower amounts of $NH_3$ and/or lower amounts of $CO_2$ as compared to the process condensate. In particular, the amount of $NH_3$ in the first partially purified flow is reduced at least 5 times as compared to the process condensate, more in particular at least 7 times, even more in particular at least 10 times, yet even more in particular at least 13 times and still more in particular at least 15 times. Typically, the first partially purified flow comprises at most 2.0% by weight $NH_3$, in particular at most 1.5% by weight $NH_3$, more particular at most 1.0% by weight $NH_3$, even more particular at most 0.7% by weight $NH_3$, yet even more particular at most 0.5% by weight $NH_3$, the % by weight being expressed compared to the total weight of the first partially purified flow. In particular, the amount of $CO_2$ is reduced in the first partially purified flow at least 10 times as compared to the process condensate, more in particular at least 30 times, even more in particular at least 50 times, yet even more in particular at least 75 times and still more in particular at least 90 times. Typically, the first partially purified flow comprises at most 1.0% by weight $CO_2$, in particular at most 0.5% by weight $CO_2$, more particular at most 0.2% by weight $NH_3$, even more particular at most 0.1% by weight $CO_2$, yet even more particular at most 0.5% by weight $CO_2$, the % by weight being expressed compared to the total weight of the first partially purified flow.

The term "second partially purified flow" as used herein, refers to an aqueous flow derived from the first partially purified flow, typically comprising lower amounts of $NH_3$ and/or lower amounts of $CO_2$ as compared to the first partially purified flow. In particular, the amount of $NH_3$ in the second partially purified flow is reduced at least 1.1 times as compared to the first partially purified flow, more in particular at least 1.2 times and even more in particular at least 1.3 times. Typically, the second partially purified flow comprises at most 1.0% by weight $NH_3$, in particular at most 0.8% by weight $NH_3$, more particular at most 0.6% by weight $NH_3$, even more particular at most 0.5% by weight $NH_3$, yet even more particular at most 0.4% by weight $NH_3$, the % by weight being expressed compared to the total weight of the second partially purified flow.

The term "purified water flow" as used herein, refers to an aqueous flow derived from the second partially purified flow, typically comprising lower amounts of $NH_3$ and/or lower amounts of $CO_2$ as compared to the second partially purified flow. In particular, the purified water flow comprises 0.0% by weight $CO_2$ and 0.0% by weight $NH_3$; the % by weight being expressed compared to the total weight of the purified water flow.

The term "hydrolyser" as used herein, refers to a device wherein urea present in an aqueous flow is hydrolysed, i.e. converted into $NH_3$ and $CO_2$.

In some embodiments, steam, in particular medium pressure (MP) steam is added to the hydrolyser, typically steam at least 10.0 barg to at most 27.0 barg, in particular at least 15.0 barg to at most 25.0 barg, more in particular at least 18.0 barg to at most 21 barg, typically at saturation temperature, like 210-217° C. In particular, the steam and aqueous flow are contacted in the hydrolyser in counter current. In particular embodiments, the hydrolyser consumes 2.5 to 3.5 t/h of MP steam. In particular embodiments, at least part of the first partially flow is provided to the hydrolyser in the top region of the hydrolyser. In particular embodiments, medium pressures steam is provided in the bottom region of the hydrolyser.

In some embodiments, the first aqueous urea solution is concentrated in a pre-evaporator to provide a concentrated second aqueous urea solution. In some embodiments, the pre evaporator is an evaporate, however, the prefix "pre-" may refer to the place of the evaporator, which is comparable to the place of a pre-evaporator in layouts for producing dried forms of urea.

In some embodiments, the first aqueous urea solution may comprise at least 40.0% by weight urea, in particular at least 45.0% by weight urea, more particular at least 55.0% by weight urea, even more particular at least 60.0% by weight urea, yet even more particular at least 65.0% by weight urea, the % by weight being expressed compared to the total weight of the first aqueous urea solution.

The term "concentrated second aqueous urea solution" as used herein, refers to an aqueous urea composition with a higher concentration of urea than the first aqueous urea solution. In particular is the concentration of urea in the concentrated second aqueous urea solution at least 1.05 times, more in particular at least 1.10 times, even more in particular at least 1.15 times yet more in particular at least 1.17 times the concentration of urea in the second partially purified flow.

In some embodiments, the concentrated second aqueous urea solution may comprise at least 60.0% by weight urea, in particular at least 65.0% by weight urea, more particular at least 70.0% by weight urea, even more particular at least 75.0% by weight urea, yet even more particular at least 80.0% by weight urea, the % by weight being expressed compared to the total weight of the concentrated second aqueous urea solution.

In some embodiments, the concentration $NH_3$ in the concentrated second aqueous urea solution is at least 5 times less, more in particular at least 7 times less, even more in particular at least 10 times less, yet even more in particular at least 13 times less and still more in particular at least 15 times less than the concentration $NH_3$ in the first aqueous urea solution. Typically, the concentrated second aqueous urea solution comprises at most 0.20% by weight $NH_3$, in particular at most 0.17% by weight $NH_3$, more particular at most 0.15% by weight $NH_3$, even more particular at most 0.13% by weight $NH_3$, yet even more particular at most 0.10% by weight $NH_3$, the % by weight being expressed compared to the total weight of the concentrated second aqueous urea solution.

In some embodiments, the target aqueous urea composition has at least an upper limit for a first contaminant, the first contaminant being comprised in the first partially purified flow; and, wherein in step g) the amount of first partially purified flow used is such that in the target aqueous urea composition at least 10% to at most 100% of the limit for the first contaminant is reached. In some, embodiments the first contaminant may also be comprised in the first aqueous urea solution and/or the concentrated second aqueous urea solution.

In some embodiments, the limit of the first contaminant is expressed as % by weight compared to the total weight of the target aqueous urea composition.

In some embodiments, the first contaminant is ammonia ($NH_3$).

In some embodiments, the upper limit for the first contaminant is 0.20% by weight, compared to the total weight of the target aqueous urea composition. Such an upper limit results in that the urea composition may be used in selective catalytic reduction (SRC) in exhaust gasses, like diesel exhaust gasses.

In some embodiments, the method further comprises the step of determining the concentration of the first contaminant in the first partially purified flow and using the concentration in determining the ratio in step g). The determined concentration of the first contaminant may be used to optimise the amount of first partially purified flow that is used to form the target aqueous urea composition and to minimise the amount of purified water flow. The more first partially purified flow the more energy is saved as less medium pressure steam needs to be added to the hydrolyser and the less low pressure steam needs to be added to the second desorption column. This may also speed up the urea production process as the reaction in the hydrolyser is typical a bottleneck.

In some embodiments, the concentration of the first contaminant is derived from measuring the pH, the conductivity and/or a first contaminant specific measurement method. In some embodiment, the concentration of the first contaminant as determined by a measuring device suitable for such concentration determination, is used to control the flow of the first partially purified flow in step g), in particular by controlling a valve downstream from the tapping point. In some embodiments, a measuring devise such as an ion specific electrode may be used.

In some embodiments, the method further comprises the step of determining the urea concentration and/or the first contaminant in the first partially purified flow and using the concentration in determining the ratio in step g). Such determination of the relevant concentrations may allow a method that can change the ratios in step g) based on fluctuations in the first partially purified flow.

In some embodiments, the method further comprises the step of determining the concentration of urea in the first aqueous urea solution and/or the second aqueous urea solution and using the concentration in determining the ratio in step g).

In some embodiments, the method comprises the step of determining the concentration of the first contaminant in the first aqueous urea solution and/or the second aqueous urea solution and using the concentration in determining the ratio in step g).

Such determination of the relevant concentrations may allow a method that can change the ratios in step g) based on fluctuations in the first aqueous urea solution and/or the second aqueous urea solution.

In some embodiments, the method comprises the step of premixing at least part of the first partially purified flow with at least part of the purified water flow to obtain a premix, before the premix is mixed with the first aqueous urea solution and/or the second concentrated aqueous urea solution.

In some embodiments, the urea concentration is determined in the premix before it is mixed with the first aqueous urea solution and/or the second concentrated aqueous urea solution, the urea concentration being used to determine the ratio in step g). This might be an alternative to determining the concentration of the first contaminant in the first partially purified flow.

In some embodiments, the concentration of the first contaminant is determined in the premix before the premix is mixed with the first aqueous urea solution and/or the second concentrated aqueous urea solution, the concentration of the first contaminant being used to determine the ratio in step g).

In some embodiments, the method comprises the step of determining the urea concentration and/or the first contaminant in the target aqueous urea composition after step g) and using this information to adjust the ratio is step g). In some embodiment, the method step is performed at least weekly, in particular at least daily.

In some embodiments, it can be assumed that the concentration of the first contaminant in the first partially purified flow is stable for at least one day, in particular at least three days, in particular at least one week, in particular at least one month, in particular at least one year, in particular forever.

In some embodiments, it can be assumed that the concentration of the first contaminant in the first aqueous urea solution and/or the second concentrated aqueous urea solution is stable for at least one day, in particular at least three days, in particular at least one week, in particular at least one month, in particular at least one year, in particular forever.

In some embodiments, the first desorption column is placed on top of the second desorption column.

In some embodiments, gasses leaving the second desorption column are fed into the first desorption column.

In some embodiments, the first desorption column and the second desorption column and share the same low pressure steam inlet, in particular a steam inlet placed in the second desorption column.

In some embodiments, the first desorption column and the second desorption column are two sections in a single desorption column divided from each other in a way that vapours can travel from the first desorption column to the second desorption column, in particular, no liquids travel directly form the second desorption column to the first desorption column, but pass though the hydrolyser first.

In some embodiments, step b) is performed in a condenser and/or flash vessel. In particular, producing a first aqueous urea solution comprising about 65.0 to 70.0% by weight urea, compared to the total weight of the first aqueous urea solution.

In some embodiments, the synthesis section may comprise an urea reactor, a carbamate condenser, a $NH_3$-stripper, a $CO_2$-stripper and/or a carbamate decomposer. In some embodiments, the synthesis section may form a reaction loop, wherein gaseous reagents may circulate.

In some embodiments, the ratio of the first partially purified flow over the purified water flow in step g) is at least 0.5, in particular at least 0.7, in particular at least 1.0, in particular at least 1.2, in particular at least 1.3, in particular at least 1.4; the ratio being expressed as weight over weight.

In some embodiments, the ratio of the first partially purified flow over the purified water flow in step g) is at least 0.5 to at most 5.5, in particular at least 0.7 to at most 5.0, in particular at least 1.0 to at most 4.0, in particular at least 1.2 to at most 3.0, in particular at least 1.3 to at most 2.5, in particular at least 1.4 to at most 2.0; the ratio being expressed as weight over weight.

In some embodiments, the ratio of first aqueous urea solution or the second urea solution over the sum of the first partially purified flow and the purified water flow, in step g) is at least 1.0, in particular at least 1.2, in particular at least 1.3, in particular at least 1.4, in particular at least 1.5, in particular at least 1.6, the ratio being expressed as weight over weight.

In some embodiments, the ratio of first aqueous urea solution or the second urea solution over the first partially purified flow the purified water flow in step g) is at least 1.0 to at most 5.5, in particular at least 1.2 to at most 5.0, in particular at least 1.3 to at most 4.0, in particular at least 1.4 to at most 3.5, in particular at least 1.5 to at most 3.0, in particular at least 1.6 to at most 2.6, the ratio being expressed as weight over weight.

The invention further foresees in a process condensate treatment plant comprising:
- a first desorption column, comprising an inlet for the process condensate and an outlet for a first partially purified flow;
- a hydrolyser comprising an inlet for the first partially purified flow and an outlet for a second partially purified flow;
- a second desorption column, comprising an inlet for the second partially purified flow and an outlet for a purified water flow.

In particular, the invention further foresees a process condensate treatment plant wherein the process condensate treatment plant comprises a tapping point for bypassing at least partially the first partially purified flow from the hydrolyser and the second desorption column.

In some embodiments, the tapping point is provided between the outlet from the first desorption column for the first partially purified flow and the inlet to the hydrolyser for the first partially purified flow. In some embodiments, the process condensate treatment plant further comprises a mixing device for mixing a urea solution with the bypassed first partially purified flow and purified water flow. In some embodiments, the process condensate treatment plant comprises a bypass for the hydrolyser, in particular a bypass for sending at least a portion of the first partially purified flow to the second partially purified flow.

Further does the invention provide in a urea production plant comprising the process condensate treatment plant according to an embodiment of the invention.

The invention will be more readily understood by reference to the following examples, which are included merely for purpose of illustration of certain aspects and embodiments of the present invention and are not intended to limit the invention.

EXAMPLES

Example 1

FIG. 1 provides a schematic overview of a lay-out that can be used to implement an embodiment of the invention.

In FIG. 1, $CO_2$ 1 and $NH_3$ 2 are provided to a synthesis section 3, reaction conditions are applied for the formation of a crude urea mixture 4. The crude urea mixture 4 is split in a condenser, belonging to the separating section 23, into a process condensate 6 and a first aqueous urea solution 5, for a typical composition see Table 1. Gaseous effluent 20 in the separating section 23 may be fed back to synthesis section 3 for further reaction.

The first aqueous urea solution 5 may be further concentrated in a pre-evaporator 15 to yield a concentrated second aqueous urea solution 14, for a typical composition see Table 1.

The process condensate 6 is fed into the top of a first desorption column 7, which is placed on top of second desorption column 8, in a way that the gaseous effluent form the second desorption column 8 is fed into the bottom of the first desorption column 7, but that no liquid can directly travel from the first desorption column 7 to the second desorption column 8. Low pressure steam 18 is fed into the bottom of the second desorption column 8. A first partially purified flow 9, 13 leaves the bottom of the first desorption column 7. A large part of the $CO_2$ and the $NH_3$ present in the process condensate 6 are removed in the first desorption column 7, as indicated in Table 1, and leaves as a gaseous effluent 21 via the top of the first desorption column 7 which may be fed back to the synthesis section 3 or separating section 23.

The first partially purified flow 9, 13 is then split in the tapping point 24. A first part of the first partially purified flow 9 is fed into the hydrolyser 10. The second part of the first partially purified flow 13 is used to dilute the second concentrated aqueous urea solution 14.

In the hydrolyser 10, medium pressure steam 19 is supplied at the bottom to decompose the urea in first partially purified flow 9 into $CO_2$ and $NH_3$. A second partially purified flow 11 leaves the hydrolyser at the bottom and is fed in the top of a second desorption column 8. In the second desorption column 8, the remaining $NH_3$ and $CO_2$ are removed, as indicated in Table 1, and a purified water flow 12 leaves the second desorption column 8 at the bottom.

In mixer 16, the purified water flow 12, the second part of the first partially purified flow 13 and the concentrated second aqueous urea solution 14 are mixed in a ratio as illustrated in Example 1 in Table 1.

TABLE 1 flow composition
Example 2

| | | | Flow | | | | |
|---|---|---|---|---|---|---|---|
| | 5 | 6 (6a + 6b) | 11 | 12 | 13(or 9) | 14 | 17 |
| Composition | | | | | | | 61.7 wt % flow 14 +22.3 wt % flow 13 +16.0 wt % flow 12 |
| P, barg | 1.2 | 2.7 | 18.7 | 4.2 | 2.7 | 0.4 | 0.0 |
| T, ° C. | 105.7 | 83.4 | 210.0 | 145.6 | 140.3 | 94.5 | 20.00 |
| wt % Urea | 69.20 | 0.3 | 0.00 | 0.00 | 0.20 | 80.97 | 50.00 |

TABLE 1-continued flow composition
Example 2

| | Flow | | | | | |
|---|---|---|---|---|---|---|
| | 5 | 6 (6a + 6b) | 11 | 12 | 13(or 9) | 14 | 17 |
|---|---|---|---|---|---|---|---|
| wt % Biuret | 0.30 | 0.0 | 0.00 | 0.00 | 0.00 | 0.33 | 0.20 |
| wt % $CO_2$ | 0.40 | 9.9 | 0.00 | 0.00 | 0.13 | 0.03 | 0.05 |
| wt % $NH_3$ | 1.10 | 9.8 | 0.40 | 0.00 | 0.55 | 0.11 | 0.19 |
| wt % $H_2O$ | 29.00 | 80.0 | 99.59 | 100.00 | 99.13 | 18.60 | 49.56 |

Example 3

Figure 2:
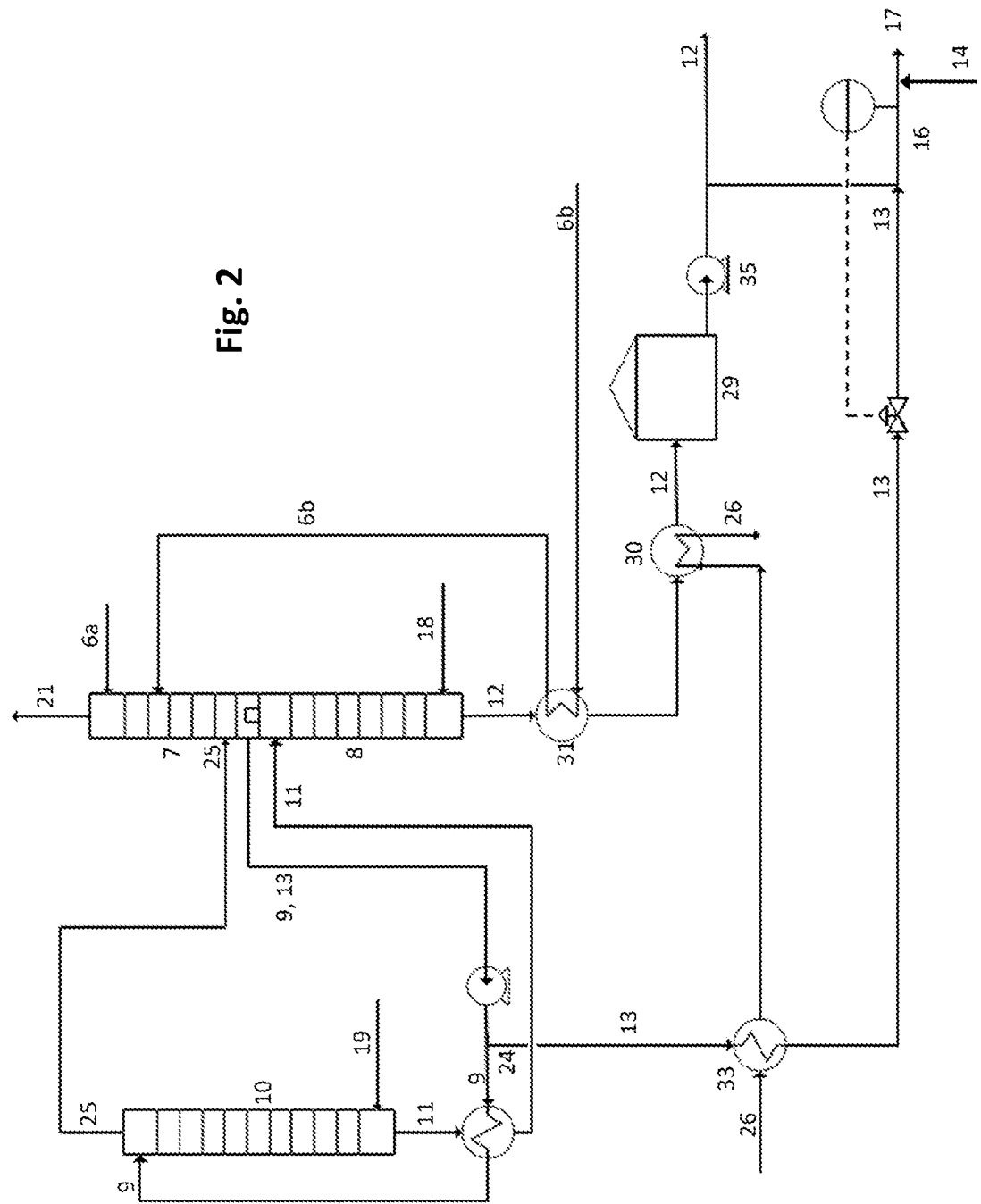
FIG. 2 depicts a practical implementation of and embodiment of a process condensate treatment plant according to the invention.

FIG. 2 depicts a practical implementation of and embodiment of a process condensate treatment plant according to the invention. Process condensate 6b and recovered process condensate 6a are provided at the top of a first desorption column 7. The first desorption column 7 is placed on top of a second desorption column 8, in a way that the gaseous effluent from the second desorption column 8 is fed into the bottom of the first desorption column 7. Low pressure steam 18 is fed into the bottom of the second desorption column 8, but that no liquid can directly travel from the first desorption column 7 to the second desorption column 8. A first partially purified flow 9, 13 leaves the bottom of the first desorption column 7. A large part of the $CO_2$ and the $NH_3$ present in the process condensate 6 are removed in the first desorption column 7, as indicated in Table 1, and leaves as a gaseous effluent 21 via the top of the first desorption column 7. The gaseous effluent 21 is fed into a condenser (not shown) to recover process condensate 6a.

The first partially purified flow 9, 13 is then split in the tapping point 24. A first part of the first partially purified flow 9 is fed into the hydrolyser 10. The second part of the first partially purified flow 13 is used to dilute a second concentrated aqueous urea solution 14, as indicated in Table 1, which may be obtained in an urea production process, in particular after a (pre-)evaporation step, like passing the urea solution through a heater with a separator placed on top.

In the hydrolyser 10, medium pressure steam 19 is supplied at the bottom to decomposed the urea in first partially purified flow 9 into $CO_2$ and $NH_3$, as indicated in Table 1. A second partially purified flow 11 leaves the hydrolyser at the bottom and is fed in the top of a second desorption column 8. The gaseous effluent 25 leaving the top of the hydrolyser 10 is fed into the bottom of the first desorption column 7. In the second desorption column 8, the remaining $NH_3$ and $CO_2$ are removed, see Table 1, and a purified water flow 12 leaves the second desorption column 8 at the bottom.

The purified water flow 12 and the second part of the first partially purified flow 13 are cooled via heat exchangers 30, 31 and 33 respectively, the heat exchangers 30 and 33 are being cooled by cool water 26. The purified water flow 12 may be stored in a tank 29, wherein a pump 35 may send it to the mixing device 16 to product the target aqueous urea composition 17.

It is to be understood that although particular embodiments and/or materials have been discussed for providing embodiments according to the present invention, various modifications or changes may be made without departing from the scope and spirit of this invention.

Example 4

This example provides a relation between the different flows and the urea concentrations.

Given that:
purified water flow 12="A" (expressed in t/h)
first partially purified flow 13="B" (expressed in t/h)
flow of second concentrated aqueous urea solution 14="C" (expressed in t/h)
flow of the target aqueous urea composition 17="D" (expressed in t/h)
weight fraction of urea in second concentrated aqueous urea solution 14 is "X" (typically 80 wt %, thus a weight fraction of 0.80)
weight fraction of urea in target aqueous urea solution 17 is "Y" (typically 50-52 wt %, thus 0.52)
Ratio (Fraction of "A" in the total A+B) between "A" and "B" is "Z" (typically 0.40-0.60)
Then:

$$D=C/X*Y \text{ (or, of course: } C=D/Y*X)$$

$$A+B=(C*X/Y)*(1-Y)-C*(1-X)$$

Further, $A=(A+B)*Z$

Thereby, $B=(A+B)*(1-Z)$

Example 5

Using the equations of Example 4, a typical example is given below:

If $D=100 t/h;$ $Y=0.52;$ and, $X=0.80$

Then $C=100/0.52*0.80=65$ t/h

Also $A+B=(65*0.80/0.52)*(1-0.52)-65*(1-0.80)=35$ t/h

And:

$A=35*0.4=14$ t/h $B=35*(1-0.4)=21$ t/h

Analysis Methods

To analyse the composition of the different flows method may be used as listed in Standard Methods for the Examination of Water and Wastewater 20th editions, edited by Lenore S. Clesceri, Arnold E. Greenberg and Andrew D. Eaton.

For the determination of the amount of urea in a flow, several options may be used, like for example the use of urease, i.e. enzymatic conversion to $NH_3$ and subsequent acidimetric titration; HPLC, i.e. standard chromatographic detection; colorimetric determination after reaction with pDAB; etc.

For the determination of the amount of $CO_2$ in a flow, distillation into barite solution and titration may be used.

For the determination of the amount of $NH_3$ in a flow, several options may be used, like the use of Nessler's reagent, Acidimetric titration, distillation into boric acid followed by titration, or Ion chromatography. Especially for continuous on-line measurement for example for process control, an ion specific electrode might be most suitable.

As used in herein, the amount of $NH_3$ does also include the amount of $NH_4^+$ dissolved in the flow. Similarly herein, the amount of $CO_2$ also includes the amount of $H_2CO_3$ dissolved in the flow.

The invention claimed is:

1. A method for providing a target aqueous urea composition with a target concentration urea, comprising the steps of:
    a) reacting $CO_2$ and $NH_3$ in a synthesis section to form a crude urea mixture;
    b) separating the crude urea mixture into a first aqueous urea solution and a process condensate using a separating section;
    c) passing the process condensate through a first desorption column to provide a first partially purified flow;
    d) passing at least part of the first partially purified flow through a hydrolyser to provide a second partially purified flow;
    e) passing the second partially purified flow through a second desorption column to provide a purified water flow;
    f) optionally concentrating the first aqueous urea solution in a pre-evaporator to provide a concentrated second aqueous urea solution; and
    g) mixing the first aqueous urea solution and/or the second concentrated aqueous urea solution with at least part of the first partially purified flow and at least part of the purified water flow in such a ratio to provide a target aqueous urea composition with the target concentration urea.

2. The method according to claim 1, wherein the target aqueous urea composition has at least an upper limit for a first contaminant, the first contaminant being comprised in the first partially purified flow; and
    wherein in step g) the amount of first partially purified flow used is so that in the target aqueous urea composition at least 10% to at most 100% of the limit for the first contaminant is reached.

3. The method according to claim 2, wherein the first contaminant is ammonia.

4. The method according to claim 2, wherein the upper limit for the first contaminant is 0.20% by weight, compared to the total weight of the target aqueous urea composition.

5. The method according to claim 2, further comprising the step of determining the concentration of the first contaminant in the first partially purified flow and using the concentration in determining the ratio in step g).

6. The method according to claim 2, further comprising the step of determining the urea concentration and/or the concentration of the first contaminant in the first partially purified flow and using the concentration in determining the ratio in step g).

7. The method according to claim 1, further comprising the step of determining the concentration of urea in the first aqueous urea solution and/or the concentrated second aqueous urea solution and using the concentration in determining the ratio in step g).

8. The method according to claim 1, wherein the first desorption column is placed on top of the second desorption column.

9. The method according to claim 1, wherein step b) is performed in a condenser.

10. The method according to claim 1, wherein the synthesis section may comprise a urea reactor, a carbamate condenser, a $NH_3$-stripper, a $CO_2$-stripper and/or a carbamate decomposer.

11. The method according to claim 1, wherein the ratio of the first partially purified flow over the purified water flow in step g) is at least 0.5; the ratio being expressed as weight over weight.

12. The method according to claim 1, wherein the ratio of the first aqueous urea solution and/or the concentrated second urea solution over the sum of the first partially purified flow and the purified water flow, in step g) is at least 1.0, the ratio being expressed as weight over weight.

13. A process condensate treatment plant comprising:
    a first desorption column, comprising an inlet for a process condensate and an outlet for a first partially purified flow;
    a hydrolyser comprising an inlet for the first partially purified flow and an outlet for a second partially purified flow;
    a second desorption column, comprising an inlet for the second partially purified flow and an outlet for a purified water flow;
wherein the process condensate treatment plant comprises a tapping point for bypassing at least partially the first partially purified flow from the hydrolyser and the second desorption column.

14. The process condensate treatment plant according to claim 13, wherein the tapping point is provided between the outlet from the first desorption column for the first partially purified flow and the inlet to the hydrolyser for the first partially purified flow.

15. A urea production plant comprising the process condensate treatment plant according to claim 13.

16. The method according to claim 11 wherein the ratio of step g) is at least 0.7.

17. The method according to claim 16 wherein the ratio of step g) is at least 1.2.

18. The method according to claim 17 wherein the ratio of step g) is at least 1.4.

19. The method according to claim 12 wherein the ratio of step g) is at least 1.2.

20. The method according to claim 19 wherein the ratio of step g) is at least 1.4.

21. The method according to claim 20 wherein the ratio of step g) is at least 1.6.

* * * * *